United States Patent
Von Hagen et al.

(10) Patent No.: US 12,359,164 B2
(45) Date of Patent: Jul. 15, 2025

(54) PROCESS FOR PRODUCING CELL CULTURE MEDIA

(71) Applicant: Merck Patent GmbH, Darmstadt (DE)

(72) Inventors: Joerg Von Hagen, Pfungstadt (DE); Nikolai Stankiewicz, Darmstadt (DE); Anke Simon, Riedstadt (DE)

(73) Assignee: Merck Patent GmbH, Darmstadt (DE)

( * ) Notice: Subject to any disclaimer, the term of this patent is extended or adjusted under 35 U.S.C. 154(b) by 1121 days.

(21) Appl. No.: 17/206,615

(22) Filed: Mar. 19, 2021

(65) Prior Publication Data

US 2021/0207079 A1    Jul. 8, 2021

Related U.S. Application Data

(63) Continuation of application No. 15/749,800, filed as application No. PCT/EP2016/001177 on Jul. 8, 2016, now abandoned.

(30) Foreign Application Priority Data

Aug. 5, 2015  (EP) ..................................... 15179817

(51) Int. Cl.
*C12N 5/00* (2006.01)

(52) U.S. Cl.
CPC ........ *C12N 5/0018* (2013.01); *C12N 2500/24* (2013.01); *C12N 2500/32* (2013.01)

(58) Field of Classification Search
CPC .............. C12N 5/0118; C12N 2500/24; C12N 2500/32
See application file for complete search history.

(56) References Cited

U.S. PATENT DOCUMENTS

| | | |
|---|---|---|
| 3,579,465 A | 5/1971 | Schmolka |
| 3,740,421 A | 6/1973 | Schmolka |
| 5,045,468 A | 9/1991 | Darfler |
| 9,994,810 B2 | 6/2018 | Von Hagen |
| 2006/0003448 A1 | 1/2006 | Fike |
| 2015/0166949 A1 | 6/2015 | Von Hagen |

FOREIGN PATENT DOCUMENTS

| | | |
|---|---|---|
| EP | 2674482 A1 | 12/2013 |
| WO | 2013185876 A1 | 12/2013 |
| WO | 2014075807 A1 | 5/2014 |

OTHER PUBLICATIONS

El-Badry M, Fathy M. Enhancement of the dissolution and permeation rates of meloxicam by formation of its freeze-dried solid dispersions in polyvinylpyrrolidone K-30. Drug Dev Ind Pharm. Feb. 2006;32(2):141-50. (Year: 2006).*
Gupta et al., Effect of lyophilization and polymer compositions on solubility of aceclofenac solid dispersions. Journal of Advanced Pharmacy Education & Research 2: 113-119 (2011) (Year: 2011).*
Khoder et al. Efficient approach to enhance drug solubility by particle engineering of bovine serum albumin. Int J Pharm. Dec. 30, 2016;515(1-2):740-748 (Year: 2016).*
International Search Report PCT/EP2016/001177 dated Oct. 5, 2016.
Claudia Synowietz and Klaus Schafer: "Chemiker-Kalender, 3rd ed.", 1984, Springer, ISBN: 978-3-540-126.
De Palma A.: "Confluent Trends in cell culture media", vol. 36, No. 3, Feb. 1, 2016 (Feb. 1, 2016), XP002762170, Retrieved from the Internet [retrieved on Sep. 15, 2016].
Dixit et al., "Lyophilization monophase solution technique for improvement of the solubility and dissolution of piroxicam", Res Pharm Sci, Jan.-Mar. 2012, 7(1): 13-21 (Year: 2012).

* cited by examiner

*Primary Examiner* — Ruth A Davis
(74) *Attorney, Agent, or Firm* — Millen, White, Zelano & Branigan, P.C.; Csaba Henter

(57) ABSTRACT

The present invention relates to a process for manufacturing dry powder cell culture media. The preparation and usage of mixed particles generated by co-lyophilisation leads to cell culture media with improved solubility without changing the chemical composition.

6 Claims, 1 Drawing Sheet

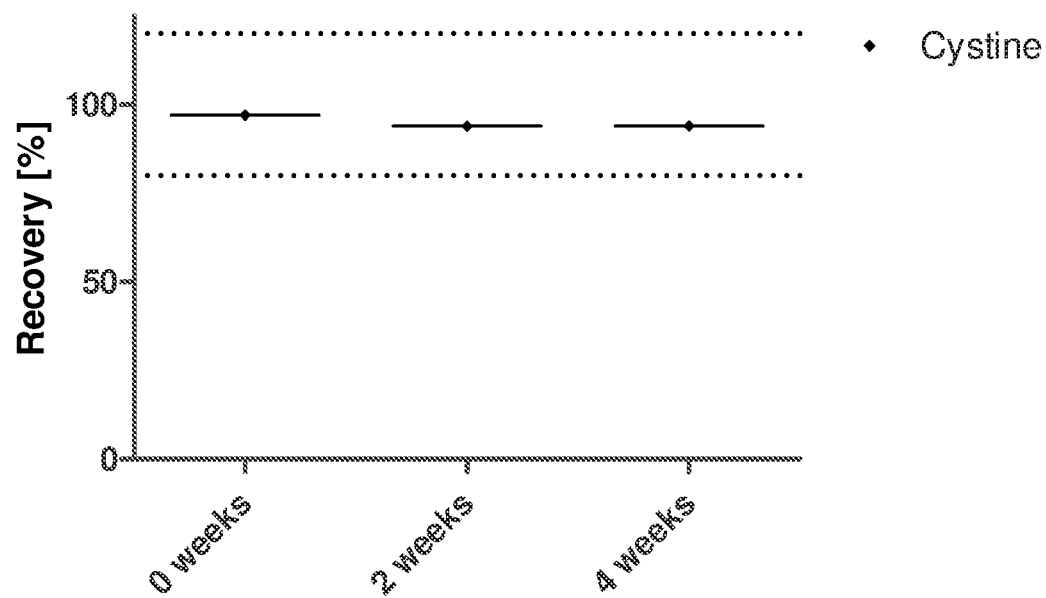

PROCESS FOR PRODUCING CELL CULTURE MEDIA

The present invention relates to a process for manufacturing dry powder cell culture media. The preparation and usage of mixed particles generated by co-lyophilisation leads to cell culture media with improved solubility without changing the chemical composition.

BACKGROUND OF THE INVENTION

Cell culture media in aqueous solution can provide an environment which supports and maintains the growth of cells and/or maintains a desired physiological cellular condition advantageous to the targeted production of certain products.

Cell culture media comprise of a complex mixture of components, sometimes more than one hundred different components, depending on the type of organism whose growth and/or targeted physiological status shall be supported.

The cell culture media required for the propagation of mammalian, insect or plant cells are typically much more complex than the media to support the growth of bacteria, yeast or fungi.

The first cell culture media that were developed consisted of undefined components, such as plasma, serum, embryo extracts, or other non-defined biological extracts or peptones. A major advance was thus made with the development of chemically defined media. Chemically defined media often comprise but are not exclusively limited to amino acids, vitamins, metal salts, antioxidants, chelators, growth factors, buffers, hormones, and many more substances known to those expert in the art.

Some cell culture media are offered as sterile aqueous liquids. The disadvantage of liquid cell culture media is their reduced shelf life and difficulties for shipping and storage. As a consequence, many cell culture media are presently offered as finely milled dry powder mixtures. They are manufactured for the purpose of dissolving in water and/or aqueous solutions and in the dissolved state are designed, often with other supplements, for supplying cells with a substantial nutrient base for growth and/or production of biopharmaceuticals from same said cells.

Most biopharmaceutical production platforms are based on fed-batch cell culture protocols. The aim typically is to develop high-titer cell culture processes to meet increasing market demands and reduce manufacturing costs. Beside the use of high-performing recombinant cell lines, improvements in cell culture media and process parameters are required to realize the maximum production potentials.

In a fed-batch process, a basal medium supports initial growth and production, and a feed medium prevents depletion of nutrients and sustains the production phase. The media are chosen to accommodate the distinct metabolic requirements during different production phases. Process parameter settings—including feeding strategy and control parameters—define the chemical and physical environments suitable for cell growth and protein production.

Optimization of the feed medium is major aspect in the optimization of a fed-batch process.

Mostly the feed medium is highly concentrated to avoid dilution of the bioreactor. The controlled addition of the nutrient directly affects the growth rate of the culture.

A limiting factor for the preparation of cell culture media from dry powder is the poor solubility of some components. Consequently it would be favourable to find a way to improve the solubility of such compounds in cell culture media.

BRIEF DESCRIPTION OF THE INVENTION

It has been found that the solubility of compounds can be improved by co-lyophilizing them with at least one other carrier compound. Those mixed particles are prepared by co-lyophilisation and can then be mixed and milled with the other components of the cell culture medium. As the solubility of the poorly soluble components is improved by co-lyophilisation, the cell culture medium treated with the method of the present invention has a better solubility compared to a cell culture medium with the same composition whose components are only mixed and milled without adding the poorly soluble components as co-lyophilisates. This solubility improvement is achieved without changing the chemical composition of the cell culture medium.

The present invention is thus directed to a method for improving the solubility of a dry powder cell culture medium with a given composition by
a) identifying the one or more poorly soluble components in the said cell culture medium
b) co-lyophilizing the one or more components identified in step a) with at least one component of said cell culture medium as carrier component
c) preparing the said dry powder cell culture medium by mixing the one or more co-lyophilisates generated in step b) with the other components of the cell culture medium and optionally milling the resulting mixture In a preferred embodiment, the one or more poorly soluble components are compounds with a solubility in water at 25° C. of less than 10 g/l.

In a preferred embodiment, the one or more carrier components are selected from the following group:
Calcium Chloride, anhydrous and hydrated forms
Di-Potassium hydrogen phosphate, anhydrous and hydrated forms
Di-Sodium Hydrogen Phosphat, anhydrous and hydrated forms
Magnesium Chloride, anhydrous and hydrated forms
Magnesium Sulfate, anhydrous and hydrated forms
Potassium chloride
Potassium Dihydrogen Phosphate
Sodium Chloride
Sodium dihydrogen phosphate, anhydrous and hydrate forms
Sodium hydrogen carbonate
D(−)-Fructose
D(−)-Mannitol
D(+)-Galactose
D(+)-Glucose, anhydrous and hydrate forms
D(+)-Mannose
Glycine
Glycyl-L-tyrosine Hydrate
L-Alanine
L-Alanyl-L-Glutamine
L-Arginine and hydrochloride forms
L-Asparagine monohydrate
L-Aspartic Acid
L-Cysteine and Hydrochloride/Hydrate forms
L-Glutamic acid
L-Glutamine
L-Histidine and hydrochloride forms
L-Hydroxyproline
L-Isoleucine L-Leucine
L-Lysine Monohydrate and hydrochloride forms
L-Methionine
L-Phenylalanine
L-Proline
L-Serine
L-Threonine
L-Tryptophan
L-Valine
mono-Sodium-L-aspartate-Monohydrate
Phospho-Tyrosine Di-Sodium Salt
Sodium L-glutamate monohydrate
HEPES_CCM
HEPES Sodium
MOPS
Choline Chloride
Poloxamer 188
Sodium acetate trihydrate
myo-Inositol
Oxalacetic acid
Succinic Acid
Pyruvic Acid Sodium Salt
alpha-Ketoglutaric Acid Disodiumsalt Dihydrate
beta-Glycerophosphoric acid disodium salt pentahydrate
or mixtures thereof In a preferred embodiment, the one or more carrier components are selected from the following group: sodium chloride, D(−)-fructose, D(−)-mannitol, D(+)-galactose, D(+)-mannose, glucose anhydrate as well as hydrated form of glucose, glycine, L-alanine, L-arginine and its hydrochloride forms, L-asparagine monohydrate, L-aspartic acid, L-cysteine and hydrochloride/hydrate forms, L-glutamic acid, L-glutamine, L-histidine and hydrochloride forms, L-isoleucine, L-leucine, L-lysine monohydrate and hydrochloride forms, L-methionine, L-phenylalanine, L-proline, L-serine, L-threonine, L-tryptophan, L-valine, mono-sodium-L-aspartate-monohydrate, sodium glutamate monohydrate, HEPES and sodium forms, MOPS, choline chloride, poloxamers like poloxamer 188, or mixtures of one or more of the said components.

In one embodiment, the one or more carrier components are compounds with a solubility in water at 25° C. of more than 10 g/l.

In a preferred embodiment, the one or more poorly soluble components are selected from the group of cystine, iron(III)citrate hydrate, iron(III)chloride hexahydrate and/or tyrosine.

In another preferred embodiment in step b) the co-lyophilisation is performed by generating an aqueous solution of the components, freezing the mixture and removing the liquid under reduced pressure.

The present invention is further directed to a process for manufacturing cell culture media by
 a) co-lyophilizing at least one component of the cell culture medium which is poorly soluble with at least one other component of the cell culture medium as carrier component.
 b) mixing the one or more co-lyophilisates generated in step a) with the other components of the cell culture medium
 c) optionally subjecting the mixture of step b) to milling In a preferred embodiment, the at least one poorly soluble component is a compound which has a solubility in water at 25° C. of less than 10 g/l.

In a preferred embodiment, the one or more poorly soluble components are selected from the group of cystine, iron(III)citrate hydrate, iron(III)chloride hexahydrate and/or tyrosine.

In a preferred embodiment, the one or more carrier components are selected from the following group: sodium chloride, D(−)-fructose, D(−)-mannitol, D(+)-galactose, D(+)-mannose, glucose anhydrate as well as hydrated form of glucose, glycine, L-alanine, L-arginine and its hydrochloride forms, L-asparagine monohydrate, L-aspartic acid, L-cysteine and hydrochloride/hydrate forms, L-glutamic acid, L-glutamine, L-histidine and hydrochloride forms, L-isoleucine, L-leucine, L-lysine monohydrate and hydrochloride forms, L-methionine, L-phenylalanine, L-proline, L-serine, L-threonine, L-tryptophan, L-valine, mono-sodium-L-aspartate-monohydrate, sodium glutamate monohydrate, HEPES and sodium forms, MOPS, choline chloride, poloxamers like poloxamer 188, or mixtures of one or more of the said components.

In a preferred embodiment, in the co-lyophilisate the amount of the component which is poorly soluble in water is between 1 and 50% (w/w) of the amount of the carrier component.

In another preferred embodiment in step a) the co-lyophilisation is performed by generating an aqueous solution of the components, freezing the mixture and removing the liquid under reduced pressure.

In another preferred embodiment, the mixture from step b) is milled in a ball mill, a pin mill, fitz mill or a jet mill.

In another preferred embodiment, the mixture from step b) is cooled to a temperature below 10° C. prior to milling.

In another embodiment, in step a) two or more different co-lyophilisates are produced, each by co-lyophilizing at least two components of the cell culture medium.

The present invention is further directed to powdered cell culture media produced by the method according to the present invention.

The present invention is further directed to powdered cell culture media comprising one or more co-lyophilisates containing at least one component which is poorly soluble in water and at least one carrier component. Preferably, the co-lyophilisates only contain one component which is poorly soluble in water and one carrier component.

In a preferred embodiment, the powdered cell culture media contain one or more co-lyophilisates comprising cystine, iron(III)citrate hydrate, iron(III)chloride hexahydrate and/or tyrosine.

In one embodiment, the powdered cell culture media comprise two or more co-lyophilisates.

DESCRIPTION OF THE INVENTION

FIG. 1 shows the stability of cystine in a DMEM F12 cell culture medium prepared by adding cystine in form of a co-lyophilisate. Further details can be found in Example 5.

A cell culture medium according to the present invention is any mixture of components which maintains and/or supports the in vitro growth of cells and/or supports a particular physiological state. It might be a complex medium or a chemically defined medium. The cell culture medium can comprise all components necessary to maintain and/or support the in vitro growth of cells or only some components so that further components are added separately. Examples of cell culture media according to the present invention are full media which comprise all components necessary to maintain and/or support the in vitro growth of cells, media supplements or feeds. In a preferred embodiment the cell culture medium is a full medium or a feed.

Typically, the cell culture media according to the invention are used to maintain and/or support the growth of cells in a bioreactor and/or to support a particular physiological state.

A mammalian cell culture medium is a mixture of components which maintain and/or support the in vitro growth of mammalian cells. Examples of mammalian cells are human or animal cells, preferably CHO cells, COS cells, I VERO cells, BHK cells, AK-1 cells, SP2/0 cells, L5.1 cells, hybridoma cells or human cells. Suitable cell culture methods are for example fed batch processes or perfusion cell culture processes.

Chemically defined cell culture media are cell culture media that do not comprise any chemically undefined substances. This means that the chemical composition of all the chemicals used in the media is known. The chemically defined media do not comprise any yeast, animal or plant tissues; they do not comprise feeder cells, serum, extracts or digests or other components which may contribute chemically poorly defined proteins to the media. Chemically undefined or poorly defined chemical components are those whose chemical composition and structure is not known, are present in varying composition or could only be defined with enormous experimental effort—comparable to the evaluation of the chemical composition and structure of a protein like albumin or casein.

A powdered cell culture medium is a cell culture medium resulting from a milling process. That means the powdered cell culture medium is a dry, particulate medium—not a liquid medium.

Cells to be cultured with the media according to the present invention may be prokaryotic cells like bacterial cells or eukaryotic cells like plant or animal cells. The cells can be normal cells, immortalized cells, diseased cells, transformed cells, mutant cells, somatic cells, germ cells, stem cells, precursor cells or embryonic cells, any of which may be established or transformed cell lines or obtained from natural sources.

Lyophilisation according to the present invention is freeze-drying by freezing the material and then reducing the surrounding pressure to allow the frozen water and optionally other volatile components in the material to sublimate directly from the solid phase to the gas phase.

As used herein, "co-lyophilised" or "co-lyophilisate" refers to a product resulting from the lyophilization, freeze-drying, cryodesiccation or vacuum drying of more than one compound in solution in the same vessel. For example, two solutions might be combined in the same vessel and the resulting combination of solutions is lyophilized together, thereby lyophilizing the components in the solutions simultaneously. Alternatively, two or more compounds, also called media components, can be dissolved in the same liquid and afterwards be lyophilised together. The resulting product of such a co-lyophilisation is a co-lyophilisate consisting of solid material that comprises a mixture of all non-volatile components that have been co-lyophilised.

An inert atmosphere is typically generated by filling the respective container or apparatus with an inert gas. Suitable inert gases are noble gases like argon or preferably nitrogen. These inert gases are non-reactive and prevent undesirable chemical reactions from taking place. According to the present invention, generating an inert atmosphere means that the concentration of oxygen is reduced below 10% (v/v) absolute, e.g. by introducing liquid nitrogen or nitrogen gas.

Different types of mills are known to a person skilled in the art.

A pin mill, also called centrifugal impact mill, pulverizes solids whereby protruding pins on high-speed rotating disks provide the breaking energy.

Pin mills are for example sold by Munson Machinery (USA), Premium Pulman (India), Hosokawa Alpine or Sturtevant (USA).

A jet mill uses compressed gas to accelerate the particles, causing them to impact against each other in the process chamber. Jet mills are e.g. sold by Sturtevant (USA), Hosokawa Alpine or PMT (Austria).

A fitz mill commercialized by Fitzpatrick (USA), uses a rotor with blades for milling.

A process that is run continuously is a process that is not run batchwise. If a milling process is run continuously it means that the media ingredients are permanently and steadily fed into the mill over a certain time.

The cell culture media which are manufactured according to the method of the present invention typically comprise at least one or more saccharide components, one or more amino acids, one or more vitamins or vitamin precursors, one or more salts, one or more buffer components, one or more co-factors and one or more nucleic acid components.

The media may also comprise sodium pyruvate, insulin, vegetable proteins, fatty acids and/or fatty acid derivatives and/or pluronic acid and/or surface active components like chemically prepared non-ionic surfactants. One example of a suitable non-ionic surfactant are difunctional block copolymer surfactants terminating in primary hydroxyl groups also called poloxamers, e.g. available under the trade name Pluronic® from BASF, Germany. Such substances are block copolymers based on ethylene oxide and propylene oxide (Polyethylene glycol (PEG)/polypropylene glycol (PPG) block copolymers). The poloxamers, CAS number 9003-11-6, to be preferably used have the general formula I

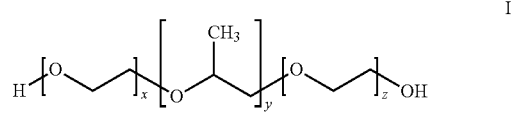

with x and z preferably independently being 2 to 130 and y preferably being 15 to 67.

Commercially available poloxamers are e.g. Pluronics® or Lutrole®, e.g., a Pluronic® solution, gel, or solid, such as Pluronic® F-127). Alternatively, the poloxamer can be made from raw materials according to methods known in the art (see, for example, U.S. Pat. Nos. 3,579,465 and 3,740,421).

Particularly preferred is Poloxamer 188 sometimes called Pluronic F 68 or Kolliphor P 188 or Lutrol F 68.

Saccharide components are all mono- or di-saccharides, like glucose, galactose, ribose or fructose (examples of monosaccharides) or sucrose, lactose or maltose (examples of disaccharides).

Examples of amino acids according to the invention are the proteinogenic amino acids, especially the essential amino acids, leucine, isoleucine, lysine, methionine, phenylalanine, threonine, tryptophane and valine, as well as the non-proteinogenic amino acids like D-amino acids.

Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin B$_9$ (Folic acid, folinic acid), Vitamin B$_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Vitamin precursors are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn. Examples are Copper(II) sulphate pentahydrate (CuSO$_4$·5H$_2$O), Sodium Chloride (NaCl), Calcium chloride (CaCl$_2$·2H$_2$O), Potassium chloride (KCl), Iron(II)sulphate, sodium phosphate monobasic anhydrous (NaH$_2$PO$_4$), Magnesium sulphate anhydrous (MgSO$_4$), sodium phosphate dibasic anhydrous (Na$_2$HPO$_4$), Magnesium chloride hexahydrate (MgCl$_2$·6H$_2$O), zinc sulphate heptahydrate.

Examples of buffers are CO$_2$/HCO$_3$ (carbonate), phosphate, HEPES, PIPES, ACES, BES, TES, MOPS and TRIS.

Examples of cofactors are thiamine derivatives, biotin, vitamin C, NAD/NADP, cobalamin, flavin mononucleotide and derivatives, glutathione, heme nucleotide phosphates and derivatives.

Nucleic acid components, according to the present invention, are the nucleobases, like cytosine, guanine, adenine, thymine or uracil, the nucleosides like cytidine, uridine, adenosine, guanosine and thymidine, and the nucleotides like adenosine monophosphate or adenosine diphosphate or adenosine triphosphate.

For all compound mentioned the compound name also includes any salts, hydrates, di-, tri- or oligomers or enantiomers. For example glucose also means glucose monohydrate, or Hepes (4-(2-hydroxyethyl) piperazine-1-ethanesulfonic acid) also means Hepes sodium salt (4-(2-Hydroxyethyl)piperazine-1-ethanesulfonic acid sodium salt).

Freezing according to the present invention means cooling to a temperature below 0° C.

The gist of the present invention is to improve the solubility of poorly soluble components of powdered cell culture media and thus the overall solubility of a cell culture medium with a given composition. Powdered cell culture media with a given composition might comprise one or several components which do not dissolve in a given amount of water or need a special treatment like elevated temperature or a long time to dissolve. It is typically not desirable to amend the overall composition of the cell culture medium to reduce the amount of the poorly soluble component or substitute it by another component.

It has been found that with the method of the present invention the solubility of a powdered cell culture medium can be improved without changing its chemical composition.

This is done by identifying in a given cell culture medium composition the one or more components which are poorly soluble and hinder easy dissolution of the dry powder medium.

A person skilled in the art of cell culture media it typically aware of the solubilities of the typical ingredients of cell culture media and can identify the poorly soluble components in a given list of ingredients.

Identification can also be done by reviewing the list of ingredients of a given composition and identifying the one or more components with the poorest solubility based on solubility data. The solubility of substances is typically known and can be found in publicly available data bases or text books, e.g. *Chemiker-Kalender*. editors Claudia Synowietz and Klaus Schäfer; 3. Edition, 2. Reprint 1992; 656 pages; Berlin, Heidelberg, New York, Tokyo; Springer 1984; ISBN 978-3-540-12652-2.

Identification can also be done experimentally by dissolving a given dry powder medium and in case of incomplete dissolution, isolating the non-dissolved particles and analysing them e.g. by NMR, mass spectrometry, elementary analysis, chromatographic methods or combinations thereof. Examples of suitable methods are ICP-OES, UPLC (e.g. for amino acids), IC. From this analysis one obtains information about the chemical composition of the non-dissolved particles and can thus identify the poorly soluble components.

Those poorly soluble components are then co-lyophilized with one or more carrier components of the cell culture medium prior to adding them to the dry powder mixture. It is possible to co-lyophilize one or more poorly soluble components with one carrier component or one poorly soluble component with one or more carrier components. Preferably, one poorly soluble component is co-lyophilized with one carrier component.

A component that is poorly soluble according to the present invention is any component of a cell culture medium whose solubility in said cell culture medium composition shall be further improved under given dissolution conditions. Poorly soluble components are often substances of which less than 10 g, especially less than 1 g, can be dissolved in 1 liter of water at 25° C. The present invention is suitable for such poorly soluble substances but can of course also be used for substances of which more than 10 g can be dissolved in 1 liter of water at 25° C. if further improvement of their solubility is needed, for example if they need to be added in quite large amounts or if the time needed for dissolving the substance is comparably long. In addition, the solubility of a substance in water can differ from its solubility in a cell culture medium composition comprising several other components. Consequently, a substance that is poorly soluble according to the present invention is preferably a substance of which less than 10 g, especially less than 1 g, can be dissolved in 1 liter of DMEM F12 cell culture medium at 25° C. The composition of DMEM F12 cell culture medium (product of Sigma Aldrich, article number D2906) is shown in the Examples. Typically the dissolution should be completed after 2 hours, preferably after 45 minutes.

Examples of poorly soluble cell culture media components are known to a person skilled in the art or are identified as described above for a given cell culture media composition. They may differ depending on the type of cell culture medium. Typical examples are: cystine, ferric citrate (iron (III) citrate hydrate), Fe(III) chloride hexahydrate and/or tyrosine. While cystine is poorly soluble in water and cell culture media, Fe(III) chloride hexahydrate is an example of a component which is sufficiently soluble in water but typically shows very poor solubility in cell culture media.

Carrier components are all cell culture media components which are no poorly soluble components and whose concentration in the cell culture medium composition is high enough so that they are present in an amount sufficient to be co-lyophilized with the poorly soluble component.

Preferably, carrier components are components that are present in the cell culture medium with a percentage of more than 3%, preferably more than 10% (w/w) of the cell culture medium. But it is also possible in certain cases to use other components as carrier components as the amount of carrier component that is needed depends on the amount of the poorly soluble component. If the poorly soluble component is present in very low amounts, also a component that is present in less than 3% (w/w) in the cell culture medium composition might be a suitable carrier component. On the other hand, if the poorly soluble component is present in large amounts, it might be necessary to choose a carrier which is present in more than 10% (w/w).

Preferably, carrier components are components of which more than 10 g, preferably more than 100 g can be dissolved in 1 liter of water or preferably DMEM-F12.

Carrier components can be salts, like sodium chloride, sugars, like glucose, amino acids like arginine or buffers like HEPES or MOPS or others like choline chloride or poloxamer.

TABLE 1 shows a list of suitable carrier components:

| Group | CAS-No. | Component | Solubility (water) PubChem Database |
|---|---|---|---|
| Inorganic Salts | 10043-52-4 | Calcium Chloride anhydrous | 745 g/l at 20° C. |
| | 10035-04-8 | Calcium chloride dihydrate | |
| | 04.11.7758 | Di-Potassium hydrogen phosphate anhydrous | 100 g/67 g water |
| | 7558-79-4 | Di-Sodium Hydrogen Phosphat Anhydrous | 7.7 g/100 ml at 20° C. |
| | 7791-18-6 | Magnesium Chloride Hexahydrate | |
| | 7487-88-9 | Magnesium Sulfate Anhydrous | 30 g/100 ml at 20° C. |
| | 10034-99-8 | Magnesium sulfate heptahydrate | |
| | 7447-40-7 | Potassium chloride | 35.5/100 g water at 25° C. |
| | 7778-77-0 | Potassium Dihydrogen Phosphate | 25 g/100 ml water at 25° C. |
| | 7647-14-5 | Sodium Chloride | 36 g/100 ml water at 25° C. |
| | 13472-35-0 | SODIUM DIHYDROGEN PHOSPHATE DIHYDRATE | |
| | 10049-21-5 | SODIUM DIHYDROGEN PHOSPHATE MONOHYDRATE | |
| | 144-55-8 | SODIUM HYDROGEN CARBONATE | 8.7 g/100 ml water at 20° C. |
| Sugars | 57-48-7 | D(−)-FRUCTOSE | 200 g/100 ml water at 25° C. |
| | 69-65-8 | D(−)-MANNITOL | 216 g/l water at 25° C. |
| | 59-23-4 | D(+)-GALACTOSE | |
| | 50-99-7 | D(+)-Glucose anhydrous | 470 g/L bei 20° C. |
| | 14431-43-7 | D(+)-Glucose Monohydrate | |
| | 3458-28-4 | D(+)-Mannose | 713 g/L bei 17° C. |
| | 50-99-7 | Glucose anhydrous | |
| Amino Acids | 56-40-6 | GLYCINE | 250 g/L bei 25° C. |
| | 658-79-7 | Glycyl-L-tyrosine Hydrate | |
| | 56-41-7 | L-ALANINE | 164 g/l water at 25° C. |
| | 39537-23-0 | L-Alanyl-L-Glutamine | |
| | 74-79-3 | L-Arginine | |
| | 1119-34-2 | L-ARGININE MONOHYDRO-CHLORIDE | |
| | 5794-13-8 | L-ASPARAGINE MONOHYDRATE | |
| | 56-84-8 | L-Aspartic Acid | 5.39 g/l water at 25° C. |
| | 52-90-4 | L-Cysteine | 277 g/l water at 25° C. |

TABLE 1-continued shows a list of suitable carrier components:

| Group | CAS-No. | Component | Solubility (water) PubChem Database |
|---|---|---|---|
| | 06.04.7048 | L-CYSTEINE HYDROCHLORIDE MONOHYDRATE | |
| | 56-86-0 | L-GLUTAMIC ACID | 8.57 g/l water at 25° C. |
| | 56-85-9 | L-GLUTAMINE | |
| | 71-00-1 | L-Histidine | 45.6 g/l water at 25° C. |
| | 5934-29-2 | L-HISTIDINE MONOHYDRO-CHLORIDE MONOHYDRATE | |
| | 51-35-4 | L-Hydroxyproline | |
| | 73-32-5 | L-ISOLEUCINE | 34.4 g/L water at 25° C. |
| | 61-90-5 | L-LEUCINE | |
| | 39665-12-8 | L-Lysine Monohydrate | |
| | 657-27-2 | L-LYSINE MONOHYDRO-CHLORIDE | >100 g/100 mlL water at 25° C. |
| | 63-68-3 | L-Methionine | 56.6 g/L water at 25° C. |
| | 63-91-2 | L-PHENYLALANINE | |
| | 147-85-3 | L-PROLINE | |
| | 56-45-1 | L-SERINE | 425 g/L water at 25° C. |
| | 72-19-5 | L-Threonine | 97 g/L water at 25° C. |
| | 73-22-3 | L-TRYPTOPHAN | 13.4 g/L water at 25° C. |
| | 72-18-4 | L-Valine | 58.5 g/L water at 25° C. |
| | 323194-76-9 | mono-Sodium-L-aspartate-Monohydrate | |
| | Pho-Tyr Di SoSalt | Phospho-Tyrosine Di-Sodium Salt | |
| | 03.04.6106 | SODIUM L-GLUTAMATE MONOHYDRATE | |
| organic Buffers | 7365-45-9 | HEPES_CCM | |
| | 75277-39-3 | HEPES Sodium | |
| | 1132-61-2 | MOPS | |
| Others | 67-48-1 | Choline Chloride | |
| | 06.11.9003 | Poloxamer 188 | |
| | 6131-90-4 | SODIUM ACETATE TRIHYDRATE | |
| | 87-89-8 | myo-Inositol | |
| | 328-42-7 | OXALACETIC ACID | |
| | 110-15-6 | Succinic Acid | 83.2 g/L water at 25° C. |
| | 113-24-6 | Pyruvic Acid Sodium Salt | |
| | 305-72-6 | alpha-Ketoglutaric Acid Disodiumsalt Dihydrate | |
| | 13408-09-8 | beta-Glycerophosphoric acid disodium salt pentahydrate | |

Also the anhydrates or hydrates as well as the hydrochlorides of the components in Table 1, if available, may be used as carrier components.

Preferred carrier components are sodium chloride, D(−)-fructose, D(−)-mannitol, D(+)-galactose, D(+)-mannose, glucose anhydrate as well as hydrated form of glucose, glycine, L-alanine, L-arginine and its hydrochloride forms, L-asparagine monohydrate, L-aspartic acid, L-cysteine and hydrochloride/hydrate forms, L-glutamic acid, L-glutamine, L-histidine and hydrochloride forms, L-isoleucine, L-leucine, L-lysine monohydrate and hydrochloride forms, L-methionine, L-phenylalanine, L-proline, L-serine, L-threonine, L-tryptophan, L-valine, mono-sodium-L-aspartate-monohydrate, sodium glutamate monohydrate, HEPES and sodium forms, MOPS, choline chloride, poloxamers like poloxamer 188, or mixtures of one or more of the said components.

Co-lyophilisation is preferably performed by co-lyophilising at least one poorly soluble component with at least one carrier component. In a preferred embodiment, one poorly soluble component is co-lyophilised with one carrier component.

The amount (weight) of the poorly soluble component that is subjected to co-lyophilisation is typically less or equal compared to the amount (weight) of the carrier component. Preferably, between 1 and 50% of the poorly soluble component are co-lyophilized with 99 to 50% of the carrier component (w/w). Most preferred, between 10 and 50% of the poorly soluble component are co-lyophilized with 90 to 50% of the carrier component (w/w). That means if e.g. 20 g of the poorly soluble component are used, about 80 g of the carrier component are used.

For co-lyophilisation, in a first step, all components to be co-lyophilised are dissolved in a solvent.

The components can be solubilised together in one solvent. Alternatively, each component can be dissolved in a separate solvent and the resulting two or more solutions of different components can then be mixed. Typically, all solutions to be mixed have the same solvent.

Suitable solvents are those in which all components are soluble. Examples of suitable solvents are organic solvents like Acetonitrile, Methanol, Ethanol, Acetone, t-Butanol, Isopropanol, DMSO or water or mixtures thereof. Preferred is water.

For the poorly soluble components, dissolution might take 1 to 24 hours. It might also be necessary to perform the dissolution under elevated temperature, typically 30 to 100° C. It is also possible to amend the pH to reach full solubility of the poorly soluble compound. This is preferably done by adding acids or bases or buffers which can be removed from the mixture during lyophilisation. Based on the known solubility of the components and the solvent that is used, a person skilled in the art is able to determine the suitable dissolution conditions and the suitable amount of poorly soluble component compared to the amount of solvent.

It is also possible to add further preferably volatile substances which support the dissolution of the poorly soluble component and which are removed from the mixture during lyophilisation. Examples are buffers, acids like HCl and bases like $NH_3$.

Once the solvent is chosen and the components have been dissolved, the resulting mixture is frozen and lyophilized to dryness. Sometimes an additional solvent like Acetonitrile, Methanol, Ethanol, Acetone, t-Butanol, Isopropanol or DMSO is added to the mixture to facilitate lyophilisation.

Lyophilisation or freeze drying is known to a person skilled in the art.

Typically lyophilisation is performed at a temperature below −20° C., preferably at around −80° C. The liquid is typically removed by applying reduced pressure. The resulting co-lyophilisate can also be called mixed particles or mixed solid. Preferably, the co-lyophilisates only contain the poorly soluble component and the carrier component.

The mixed solid is then preferably milled, e.g. in a ball mill, to generate particles of homogenous size. The resulting particles typically have a particle size below 200 μm. Preferred are particle sizes below 100 μm. Favourable particle sizes are between 15 μm and 100 μm.

The milled co-lyophilisate can then be subjected to analytical methods to determine the concentration of the components in the co-lyophilisate. Examples of suitable methods are ICP-OES, UPLC (e.g. for amino acids), NMR, IC or LC-MS.

The final co-lyophilisate can then be stored or used for the production of cell culture media.

For the latter, a suitable amount of the co-lyophilisate is mixed with the other components of the cell culture medium. It is also possible to generate two or more co-lyophilisates and mix two or more co-lyophilisates with the other components of the cell culture medium. The mixing of the components is known to a person skilled in the art of producing dry powdered cell culture media. Preferably, all components are thoroughly mixed so that all parts of the mixture have nearly the same composition. The higher the uniformity of the composition, the better the quality of the resulting medium with respect to homogenous cell growth.

Afterwards, the mixture is preferably milled.

The milling can be performed with any type of mill suitable for producing powdered cell culture media. Typical examples are ball mills, pin mills, fitz mills or jet mills. Preferred is a pin mill, a fitz mill or a jet mill, very preferred is a pin mill.

A person skilled in the art knows how to run such mills.

A large scale equipment mill with a disc diameter of about 40 cm is e.g. typically run at 1-6500 revolutions per minute in case of a pin mill, preferred are 1-3000 revolutions per minute.

The milling can be done under standard milling conditions resulting in powders with particle sizes between 10 and 300 μm, most preferably between 25 and 100 μm.

Preferably, all components of the mixture which is subjected to milling are dry. This means, if they comprise water, they do only comprise water of crystallization but not more than 10%, preferably not more than 5% most preferred not more than 2% by weight of unbound or uncoordinated water molecules. The medium resulting from milling such dry component is also called dry powdered cell culture medium.

In a preferred embodiment, the milling is performed in an inert atmosphere. Preferred inert protective gas is nitrogen.

In another preferred embodiment, all components of the mixture are freezed prior to milling. The freezing of the ingredients prior to the milling can be done by any means that ensures a cooling of the ingredients to a temperature below 10° C. and most preferably below −20° C. In a preferred embodiment the freezing is done with liquid nitrogen. This means the ingredients are treated with liquid nitrogen, for example by pouring liquid nitrogen into the container in which the ingredients are stored prior to introduction into the mill. In a preferred embodiment, the container is a feeder. If the container is a feeder the liquid nitrogen is preferably introduced at the side or close to the side of the feeder at which the ingredients are introduced.

Typically the ingredients are treated with the liquid nitrogen over 2 to 20 seconds.

Preferably the cooling of the ingredients is done in a way that all ingredients that enter into the mill are at a temperature below 10° C., most preferred below −20° C.

In a preferred embodiment, all ingredients are put in a container from which the mixture is transferred in a feeder, most preferred in a metering screw feeder. In the feeder the ingredients are sometimes further mixed—depending on the type of feeder—and additionally cooled. The freezed mixture is then transferred from the feeder to the mill so that the mixture which is milled in the mill preferably still has a temperature below 10° C., more preferred below −20° C.

Typically the blending time, that means the residence time of the mixture of ingredients in the feeder is more than one minute, preferably between 15 and 60 minutes.

A metering screw feeder, also called dosage snail, is typically run at a speed of 10 to 200 revolutions per minute, preferably it is run at 40 to 60 revolutions per minute.

Typically, the temperature of the mill is kept between −50 and +30° C. In a preferred embodiment, the temperature is kept around 10° C.

The oxygen level during milling preferably is below 10% (v/v).

The process can be run e.g. batch-wise or continuously. In a preferred embodiment the process according to the present invention is done continuously by, over a certain time, permanently filling the mixture of ingredients into a feeder for cooling and permanently filling cooled mixture from the feeder into the mill.

It has been found that in contrast to other production processes the process according to the present invention provides dry powder cell culture media with an improved solubility compared to cell culture media with the same composition that have been produced without the use of co-lyophilisates.

The present invention is further directed to a dry cell culture medium comprising at least one co-lyophilisate. Such medium is obtainable by the process according to the present invention.

Preferably, the cell culture medium comprises 1 to 10 different co-lyophilisates.

For use of the powdered media a solvent, preferably water (most particularly distilled and/or deionized water or purified water or water for injection) or an aqueous buffer is added to the media and the components are mixed until the medium is totally dissolved in the solvent.

The solvent may also comprise saline, soluble acid or base ions providing a pH range of 1.0-14.0, stabilizers, surfactants, preservatives, and alcohols or other polar organic solvents.

It is also possible to add further substances like buffer substances for adjustment of the pH, fetal calf serum, sugars etc., to the mixture of the cell culture medium and the solvent. The resulting liquid cell culture medium is then contacted with the cells to be grown or maintained.

The present invention is thus further directed to a process for culturing cells by
a) providing a cell culture medium produced according to the present invention
b) mixing said cell culture medium with water or an aqueous buffer
c) mixing the cells to be cultured with the cell culture medium of step b) in a bioreactor
d) incubating the mixture of step c)

A bioreactor is any container, vessel, bag or tank in which cells can be cultured. Incubation is typically done under suitable conditions like suitable temperature, osmolality, aeration, agitation etc. A person skilled in the art is aware of suitable incubation conditions for supporting and/or maintaining the growth/culturing of cells.

By using the co-lyophilisates for media production the overall amount of the media components and thus the overall media composition remains the same as outlined in the recipe, but as the poorly soluble components are combined with the carrier components the overall solubility of the dry powder mixture is significantly higher compared to a dry powder mixture prepared without the use of co-lyophilisates. By using the method of the invention, typically, the solubility of the poorly soluble component can be increased by at least 50%. Preferably, it is increased by at least 100%, which means that by using co-lyophilisates at least the double amount of a poorly soluble component is soluble in the same liquid cell culture media composition compared to the use of the poorly soluble substance as such.

The present invention is further directed to a method for improving the solubility of a compound in water by co-lyophilizing the said compound with a carrier compound. The carrier compound preferably is a compound of which more than 10 g are soluble in 1 l of water.

The carrier compound should be a compound that does not negatively influence the further use of the poorly soluble compound whose solubility shall be improved.

Preferably, the carrier compound is a salt or a sugar. Examples of suitable salts are sodium chloride, potassium chloride, calcium chloride ($CaCl_2 \cdot 2H_2O$), magnesium chloride ($MgCl_2$) or magnesium sulphate ($MgSO_4$). Most preferred is sodium chloride.

Typically, between 1 and 50% of the poorly soluble compound are co-lyophilized with 99 to 50% of carrier compound (w/w). Most preferred, between 10 and 50% of the poorly soluble compound are co-lyophilized with 90 to 50% of the carrier compound (w/w).

The present invention is further illustrated by the following examples, however, without being restricted thereto.

The entire disclosure of all applications, patents, and publications cited above and below and of corresponding EP 15179817.0 filed Aug. 5, 2015, are hereby incorporated by reference.

EXAMPLES

The following examples represent practical applications of the invention.

Composition of DMEM F12 cell culture medium (Sigma Aldrich article number D2906), dry powder, composition in [g/L]:

Inorganic Salts
  $CaCl_2$: 0.1166
  $CuSO_4 \cdot 5H_2O$ 0.0000013
  $Fe(NO_3)_3 \cdot 9H_2O$ 0.00005
  $FeSO_4 \cdot 7H_2O$ 0.000417
  $MgCl_2 \cdot 6H_2O$ 0.0612
  $MgSO_4$ 0.04884
  KCl 0.3118
  NaCl 6.996
  $Na_2HPO_4$ 0.07102
  $NaH_2PO_4$ 0.0543
  $ZnSO_4 \cdot 7H_2O$ 0.000432
Amino Acids
  L-Alanine 0.00445
  L-Arginine·HCl 0.1475
  L-Asparagine·$H_2O$ 0.0075
  L-Aspartic Acid 0.00665
  L-Cystine·2HCl 0.01756
  L-Cysteine·HCl·$H_2O$ 0.03129
  L-Glutamic Acid 0.00735
  L-Glutamine 0.365
  Glycine 0.01875
  L-Histidine·HCl·$H_2O$ 0.03148
  L-Isoleucine 0.05447
  L-Leucine 0.05905
  L-Lysine·HCl 0.09125
  L-Methionine 0.01724
  L-Phenylalanine 0.03548
  L-Proline 0.01725
  L-Serine 0.02625

L-Threonine 0.05345
L-Tryptophan 0.00902
L-Tyrosine·2Na·2H$_2$O 0.05579
L-Valine 0.05285
Vitamins
  D-Biotin 0.0000035
  Choline Chloride 0.00898
  Folic Acid 0.00266
  myo-Inositol 0.0126
  Niacinamide 0.00202
  D-Pantothenic Acid·½Ca 0.00224
  Pyridoxal·HCl 0.002
  Pyridoxine·HCl 0.000031
  Riboflavin 0.000219
  Thiamine·HCl 0.00217
  Vitamin B12 0.00068
Other
  D-Glucose 3.15
  HEPES 3.5745
  Hypoxanthine 0.0021
  Linoleic Acid 0.000042
  Putrescine·2HCl 0.000081
  Pyruvic Acid·Na 0.055
  DL-Thioctic Acid 0.000105
  Thymidine 0.000365
Add
  NaHCO$_3$ 1.2

1. Co-Lyophilisation—General Procedure:

Variant 1:

The poorly soluble component is dissolved in ultrapure water (e.g. Milli-Q water) with stirring and if necessary at elevated temperature.

The carrier component is also dissolved in ultrapure water (e.g. Milli-Q water).

Both solutions are combined under stirring.

Variant 2:

The carrier component is dissolved in ultrapure water (e.g. Milli-Q water). The poorly soluble component is added with stirring. The mixture is agitated and if necessary also heated until dissolution of the poorly soluble component.

In both variants, the concentration of the components, the dissolutions times and the temperatures need to be adjusted to the components to be dissolved. A person skilled in the art is able to do so.

For lyophilisation, the solution prepared according to variant 1 or 2 is poured in suitable containers (e.g. Lyoguards) and put in the freeze-dryer. Depending on the composition of the solution, it is cooled to about −45° C. within 4 to 12 hours. The condensator is cooled to −90° C. Then vacuum is applied (0.18 mbar) and the solution is dried at −45° C. for 6 hours. Then, during drying, the temperature is adjusted to about −30° C. for about 24 hours, to −20° C. for another 24 hours and finally to about 0° C. for another 12 hours. Final drying is performed under minimal vacuum (0.003 mbar) at a temperature of about 20° C. for 4 to 12 hours.

The time and the temperature gradient can be adjusted depending on the volume of solution to be dried.

2. Co-Lyophilisates:

The following co-lyophilisates are prepared:

a) Iron (III) Citrate Hydrate with Sodium Chloride
  Fe(III) citrate hydrate (CAS 207399-12-0)
  Solubility: 5 g/l H$_2$O at 25° C., but dissolution is very slow The co-lyophilisate of iron (III) citrate hydrate and sodium chloride contains 10% (w/w) iron (III) citrate hydrate and 90% sodium chloride.

b) Cystine with Arginine
  L-cystine (CAS 56-89-3)
  Solubility: nearly insoluble in water at 25° C.
  The following co-lyophilisates have been prepared:
  23% (w/w) cystine and 77% (w/w) arginine
  10% (w/w) cystine, 30% (w/w) arginine and 60% (w/w) sodium chloride 25% (w/w) cystine and 75% (w/w) arginine 3. Cell Culture Media Production The above co-lyophilisates are used for the preparation of a chemically defined cell culture media for Chinese hamster ovary cells.

By using the co-lyophilisates the overall amount of components still remains the same as outlined in the recipe.

All ingredients of the medium including the co-lyophilisates are mixed, and milled using a dosage snail and a pin mill. In the dosage snail the ingredients are treated with liquid nitrogen.

The milling is performed under the following conditions:
Temperature—mill: 10° C.
Oxygen level: below 10% absolute
Rpm—Mill: up to 2800 1/min
Blending time: 30 min
Rpm dosage snail: 40 1/min The resulting powdered cell culture medium is suitable for the culture of CHO (Chinese Hamster Ovary) cells.

4. Application Data a) Solubility of Iron(III) Citrate Hydrate

The co-lyophilisate of iron(III) citrate hydrate and sodium chloride (preparation see above) is used in combination with DMEM-F12. Dissolution of dry powder DMEM-F12 produced according to the art (with added iron(III) citrate hydrate—raw material) without co-lyophilisate and with added iron(III) citrate hydrate in form of a co-lyophilisate with sodium chloride is compared. The result is shown in Table 2. As standard raw material iron(III) citrate hydrate can only be present in DMEM-F12 to a maximal concentration of 0.002 g/L. The addition of more iron(II) citrate hydrate leads to incomplete dissolution of the medium. In contrast to this, if iron(III) citrate hydrate is added in form of a co-lyophilisate, DMEM-F12 comprising up to 30 g/L of iron(III) citrate hydrate can still be completely dissolved in water.

TABLE 2

| Type | Substance | Max. solubility in DMEM-F12 at 22° C. |
|---|---|---|
| Raw Material | Iron(III) Citrate Hydrate | 0.002 g/L |
| Lyophilisate Version | Iron(III) Citrate Hydrate-NaCl Lyophilisate | >30 g/L | b) Solubility of Cystine

The co-lyophilisates of cystine and arginine and cystine and arginine/sodium chloride (preparation see above) are used in combination with Cellvento® CHO 200 (Merck KGaA, Germany). Dissolution of dry powder Cellvento® CHO 200 produced according to the art (with added cystine—raw material) without co-lyophilisate and with added cystine in form of a co-lyophilisate with arginine and arginine/sodium chloride is compared. The result is shown in Table 3. As standard raw material cystine can only be present in Cellvento® CHO 200 to a maximal concentration of below 0.1 g/L. The addition of more cystine leads to incomplete dissolution of the medium. In contrast to this, if cystine is added in form of a co-lyophilisate, Cellvento®

CHO 200 comprising up to 0.5 g/L of cystine can still be completely dissolved in water.

TABLE 3

| Type | Substance | Max. Solubility in CHO200 at 22° C. |
|---|---|---|
| Raw Material | L-Cystine | <0.1 g/L |
| Lyophilisate Version | Arg Lyophilisate 23% | >0.5 g/L |
| | Arg/NaCl Lyophilisate 10% | >0.5 g/L |
| | Arg Lyophilisate 25% | >0.5 g/L |

5. Stability

DMEM F12 cell culture medium comprising cystine in form of a co-lyophilisate (25% (w/w) cystine and 75% (w/w) arginine) is dissolved in water according to standard preparation instructions.

The liquid medium is stored at 2 to 8° C. The cystine content is determined by UPLC after 2 and 4 weeks. The results are shown in FIG. 1. No significant reduction of the cystine content can be observed, indicating that cystine remains solubilized in the liquid medium over time.

The invention claimed is:

1. A method for improving the solubility of a dry powder cell culture mixture for preparation of an aqueous cell culture medium comprising one or more poorly soluble components selected from the group consisting of cystine and tyrosine, comprising
   a) co-lyophilizing amounts of the poorly soluble components of said cell culture medium which are at least partially insoluble in the final aqueous culture medium prepared without co-lyophilization of the poorly soluble components, with one or more other components of said cell culture medium as a carrier component, and
   b) preparing said dry powder cell culture mixture by mixing the one or more co-lyophilizates generated in step a) with the other components of the cell culture medium, whereby the dry powder mixture is obtained, and
   c) optionally milling the resulting mixture,
whereby the solubility of the poorly soluble component or components in an aqueous cell culture medium prepared by combining the dry powder mixture with an aqueous solvent is increased by at least 50% as compared to the solubility of the poorly soluble component or components in an aqueous cell culture medium prepared by combining a dry powder mixture of the amounts of the same components prepared without co-lyophilization.

2. The method of claim 1, wherein the one or more carrier components are selected from the group consisting of:
Calcium Chloride, anhydrous and hydrated forms
Di-Potassium hydrogen phosphate, anhydrous and hydrated forms
Di-Sodium hydrogen phosphate, anhydrous and hydrated forms
Magnesium chloride, anhydrous and hydrated forms
Magnesium sulfate, anhydrous and hydrated forms
Potassium chloride
Potassium dihydrogen phosphate
Sodium Chloride
Sodium dihydrogen phosphate, anhydrous and hydrate forms
Sodium hydrogen carbonate
D(−)-Fructose
D(−)-Mannitol
D(+)-Galactose
D(+)-Glucose, anhydrous and hydrate forms
D(+)-Mannose
Glycine
Glycyl-L-tyrosine Hydrate
L-alanine
L-Alanyl-L-Glutamine
L-Arginine and hydrochloride forms
L-Asparagine monohydrate
L-Aspartic Acid
L-Cysteine and Hydrochloride/Hydrate forms
L-Glutamic acid
L-Glutamine
L-Histidine and hydrochloride forms
L-Hydroxyproline
L-Isoleucine
L-Leucine
L-Lysine Monohydrate and hydrochloride forms
L-Methionine
L-Phenylalanine
L-Proline
L-Serine
L-Threonine
L-Tryptophan
L-Valine
Mono-sodium-L-aspartate-monohydrate
Phospho-Tyrosine Di-Sodium Salt
Sodium L-glutamate monohydrate
HEPES_CCM
HEPES Sodium
MOPS
Choline Chloride
Sodium acetate trihydrate
myo-Inositol
Oxalacetic acid
Succinic Acid
Pyruvic Acid Sodium Salt
alpha-Ketoglutaric Acid disodium salt Dihydrate
beta-Glycerophosphoric acid disodium salt pentahydrate
   or mixtures thereof.

3. The method of claim 1, wherein the one or more carrier components are selected from the group consisting of
sodium chloride,
D(−)-fructose,
D(−)-mannitol,
D(+)-galactose,
D(+)-mannose,
glucose anhydrate and hydrated forms thereof,
glycine,
L-alanine,
L-arginine and hydrochloride forms thereof,
L-asparagine monohydrate,
L-aspartic acid,
L-cysteine and hydrochloride/hydrate forms thereof,
L-glutamic acid,
L-glutamine,
L-histidine and hydrochloride forms thereof,
L-isoleucine,
L-leucine,
L-lysine monohydrate and hydrochloride forms thereof,
L-methionine,
L-phenylalanine,
L-proline,
L-serine,
L-threonine,
L-tryptophan,
L-valine, mono-sodium-L-aspartate-monohydrate,
sodium glutamate monohydrate,
HEPES and sodium forms thereof,
MOPS, and
choline chloride,
or mixtures thereof.

4. The method of claim 1, wherein the amount of the component or components selected from the group consisting of cystine and tyrosine is between 1 and 50% (w/w) of the amount of the carrier component.

5. The method of claim 1, wherein in step a) the co-lyophilisation is performed by generating an aqueous solution of the components, freezing the mixture and removing the liquid under reduced pressure.

6. The method of claim 1, wherein the cell culture medium is a chemically defined medium.

* * * * *